United States Patent
Altshuler

(10) Patent No.: US 11,395,756 B2
(45) Date of Patent: Jul. 26, 2022

(54) HAND SUSPENSION FIXTURE

(71) Applicant: Edward Lafe Altshuler, Erie, CO (US)

(72) Inventor: Edward Lafe Altshuler, Erie, CO (US)

(*) Notice: Subject to any disclaimer, the term of this patent is extended or adjusted under 35 U.S.C. 154(b) by 323 days.

(21) Appl. No.: 16/882,669

(22) Filed: May 25, 2020

(65) Prior Publication Data

US 2020/0281756 A1 Sep. 10, 2020

Related U.S. Application Data

(63) Continuation of application No. 15/332,077, filed on Oct. 24, 2016, now abandoned.

(60) Provisional application No. 62/245,963, filed on Oct. 23, 2015.

(51) Int. Cl.
*A61F 5/37* (2006.01)

(52) U.S. Cl.
CPC .................. *A61F 5/3761* (2013.01)

(58) Field of Classification Search
CPC .......... A61F 5/3761; A61F 5/048; A61F 5/04; A61F 5/37; A61F 5/40; A61F 2013/00157; A61G 7/065; A61G 7/075; A61G 7/05; A61G 13/1205; A61G 13/124; A61G 13/12; A61G 13/0036; A61G 13/0045; A63B 23/16
See application file for complete search history.

(56) References Cited

U.S. PATENT DOCUMENTS

| | | | |
|---|---|---|---|
| 2,584,203 A | 10/1949 | Hart | |
| 2,783,758 A | 6/1957 | Trott | |
| 3,583,397 A | 6/1971 | Baddour | |
| 3,618,214 A | 11/1971 | Armstrong | |
| 4,445,506 A * | 5/1984 | Johansson | A61F 5/04 D24/140 |
| 4,809,688 A | 3/1989 | Aymerica del Valle et al. | |
| 5,609,595 A | 3/1997 | Pennig | |
| 5,735,806 A * | 4/1998 | Leibovic | A61F 5/04 24/115 M |
| 6,811,451 B2 * | 11/2004 | Mase | H01R 13/4362 439/752 |
| 7,207,532 B1 | 4/2007 | Roberts et al. | |
| 7,771,378 B2 * | 8/2010 | Price | A61F 5/3761 128/880 |
| 8,540,656 B1 * | 9/2013 | Powlan | A61F 5/3761 602/32 |
| 2003/0220595 A1 | 11/2003 | Lambert | |
| 2011/0178449 A1 | 7/2011 | Foote | |

FOREIGN PATENT DOCUMENTS

FR 2632184 A1 6/1988

* cited by examiner

*Primary Examiner* — Camtu T Nguyen

(74) *Attorney, Agent, or Firm* — Kenneth Altshuler

(57) ABSTRACT

Described is a hand suspension fixture for recovering from skin grafts on human hands. The hand suspension fixture generally comprises five retention fixtures each adapted to connect to one of five flexible members at a first end. At a second end, each of the five flexible members can be attached to a distal end of five respective human finger tips, such as the finger's distal digits. The human hand is adapted to hang from the five flexible members whereby the five retention fixtures are spaced apart to splay the five fingers (thumb included) when the human hand is hanging from the suspension fixture.

18 Claims, 6 Drawing Sheets

HAND SUSPENSION FIXTURE

CROSS-REFERENCE TO RELATED APPLICATIONS

This application claims priority to and the benefit of U.S. patent application Ser. No. 15/332,077, entitled Hand Suspension Fixture, filed on Oct. 24, 2016, which claims priority to and the benefit of U.S. Provisional Patent Application No.: 62/245,963, entitled: Hand Suspension Fixture, filed on Oct. 23, 2015 the entire disclosure of which is hereby incorporated by reference.

BACKGROUND OF THE INVENTION

1. Field of the Invention

The present invention relates generally to an apparatus for recovering from skin grafts and more specifically to skin grafts on human hands.

2. Description of Related Art

When suffering from burns, victims generally receive care that incorporates skin grafts from a healthy part of the body to the burned area with the hopes that the transplanted skin will grow over the area that lost skin. During a skin graft, a skin cutting instrument known as a dermatome shaves a uniform layer of healthy skin from an area of the body usually hidden by clothing. The burnt area is typically debrided of the dead skin, i.e., the dead skin is removed, and the grafted skin placed on damaged area. The grafted skin placed on the area in need of covering is held in place by a dressing and stitches or staples. After 36 hours the grafted skin starts to grow blood vessels when the graft is successful. Due to the fragile nature of healing skin, patients are immobilized. Ideally, healing areas need to be free from body weight pressing against the grafted skin or contact with other body parts. Unfortunately, a patient with large areas of skin grafts rest on hospital beds, which endangers the skin graft from successfully taking to the burn area.

It is to improvements directed to recovering from skin grafts and more specifically to skin grafts on human hands that both methods and apparatus are disclosed herein.

SUMMARY OF THE INVENTION

The present invention relates generally to an apparatus assisting with recovery from skin grafts and more specifically to skin grafts on human hands.

One embodiment of the present invention can therefore comprise a hand suspension fixture comprising: five retention fixtures each adapted to connect to one of five flexible members at a first end; at a second end, each of the five flexible members adapted to be attached to essentially a distal end of five respective human digits of a human hand; the human hand adapted to hang from the five flexible members; the five retention fixtures spaced apart to splay (spread apart) the five human digits when the human hand is hanging from the suspension fixture.

Aspects of the embodiment are further contemplated wherein the five retention fixtures are independently attached to the suspension fixture. Other aspects are contemplated wherein each of the five retention fixtures are flexibly positionable to the suspension fixture. Moreover, each of the five retention fixtures can be adapted to be fixed in place to the suspension fixture via a respective knurled bolt. Aspects of the embodiment are further contemplated wherein the five retention fixtures are arranged in an arc on the suspension fixture. Yet other aspects are contemplated that the suspension fixture is adapted to be connected to a stand. Indeed other aspects contemplate that the flexible members are selected from a group comprising of metal cable, polymer cable, wire, or some other line that fulfills the purpose of handing a hand by the end of the fingers. And, other embodiments contemplate that each of the retention fixtures possess a hook adapted to receive a loop on the first end of the flexible members. Embodiments of the invention contemplate that the flexible members possess a retaining feature adapted to attach to a human digit.

Other embodiments of the present invention may additionally provide a hand suspension fixture comprising at least two retention fixtures each adapted to connect to one of two flexible members at a first end; the two flexible members each adapted to connect to a human digit from a common human hand; the human hand adapted to hang from the at least two flexible members; the at least two flexible members spaced apart to splay the at least two human digits when the human hand is hanging from the suspension fixture. Other aspects of the present invention contemplate enough flexible members to accommodate all digits on at least one human hand. The hand suspension fixture is adapted to connect to a boom stand. The hand suspension fixture providing a means for moving the retention fixtures horizontally along the hand suspension fixture. The hand suspension fixture providing a means for locking the retention fixtures in place. Each retention fixture providing a means for moving towards or away from the human hand relative to where a human hand is intended to hang. Each retention fixture providing a means for connecting to a flexible member that connects to a human distal phalange.

DETAILED DESCRIPTION

Figure 1:
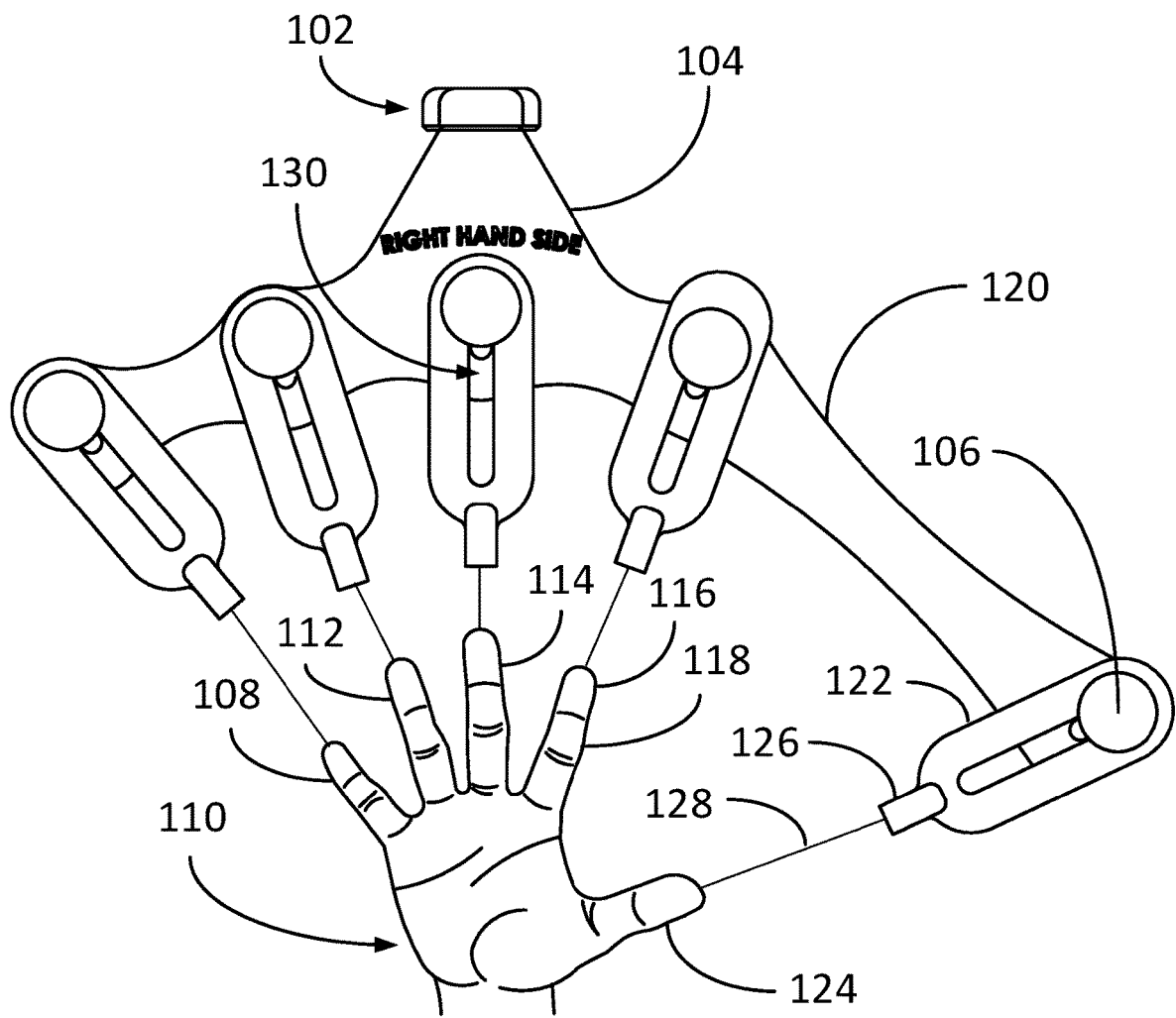
FIG. 1 is an illustration of a hand suspension fixture hanging a human hand in accordance with an embodiment of the present invention.

Initially, this disclosure is by way of example only, not by limitation. Thus, although the instrumentalities described herein are for the convenience of explanation, shown and described with respect to exemplary embodiments, which generally include, but are not limited to, supporting (hanging) a human hand via fingers in a way that splays the fingers. It will be appreciated that the principles herein may be applied equally in other types of situations involving similar uses of a suspension fixture to hold an appendage like a hand splayed and suspended consistent with the scope and spirit of the present invention.

Embodiments in the present invention are generally directed to a hand suspension fixture that provides benefit to healing a burn victim's hand. As illustratively depicted in FIG. 1, a hand suspension fixture 104 embodiment is shown suspending a human hand 110 with the fingers 118 and thumb 124 splayed open. More specifically, the hand suspension fixture 104 comprises five retention fixtures 122 each connected to one of five flexible members 128, such as metal wire, nylon cable, fishing line, and the like, at one end. At the other end, each of the five flexible members 128 are attached to essentially five respective human digits 108, 112, 114, 118, 124. Certain embodiments contemplate essentially the distal end of a human digit being along the distal phalange of the digit. Other embodiments contemplate the fingers 118 being supported closer to the palm of the hand 110. As shown, the human hand 110 is hanging from the hand suspension fixture 104 in such a way that the fingers 118 are spaced apart to splay the five fingers 118 apart from one another when hanging from the suspension fixture 104. In this way, a hand 110 that has been wrapped with new skin will heal without being touched by adjacent fingers 118 while in an essentially immobile position.

In this particular embodiment the hand suspension fixture 104 can be held at a hand suspension fixture support 102 by a boom stand, a flexible line hanging from a fixture or ceiling, or some other way that can position the hand suspension fixture 104 to hang a human hand 110 as shown in FIG. 1. The hand suspension fixture 104, as shown in this embodiment, has an arc shaped support plane 120 that facilitates the rotation of each of the five retention fixtures 122 via pivot locking mechanisms 106. Certain embodiments contemplate the pivot locking mechanism 106 being knurled bolts, nuts, quick releases, and the like that can be tightened in place. As shown in this embodiment, each retention fixture 122 possesses a retention fixture slot 130 that provides the appropriate adjustment to hang each finger 118 in a desired position. Once in the desired position, the retention fixture 122 can be locked in place by tightening the pivot locking mechanism 106. Other embodiments contemplate the pivot mechanisms 106 being free to rotate along the arc shaped support plane 120 whereby the adjustment to splay the fingers 118 in a desired way can be accomplished at the flexible member attachment location 126.

Figure 2:
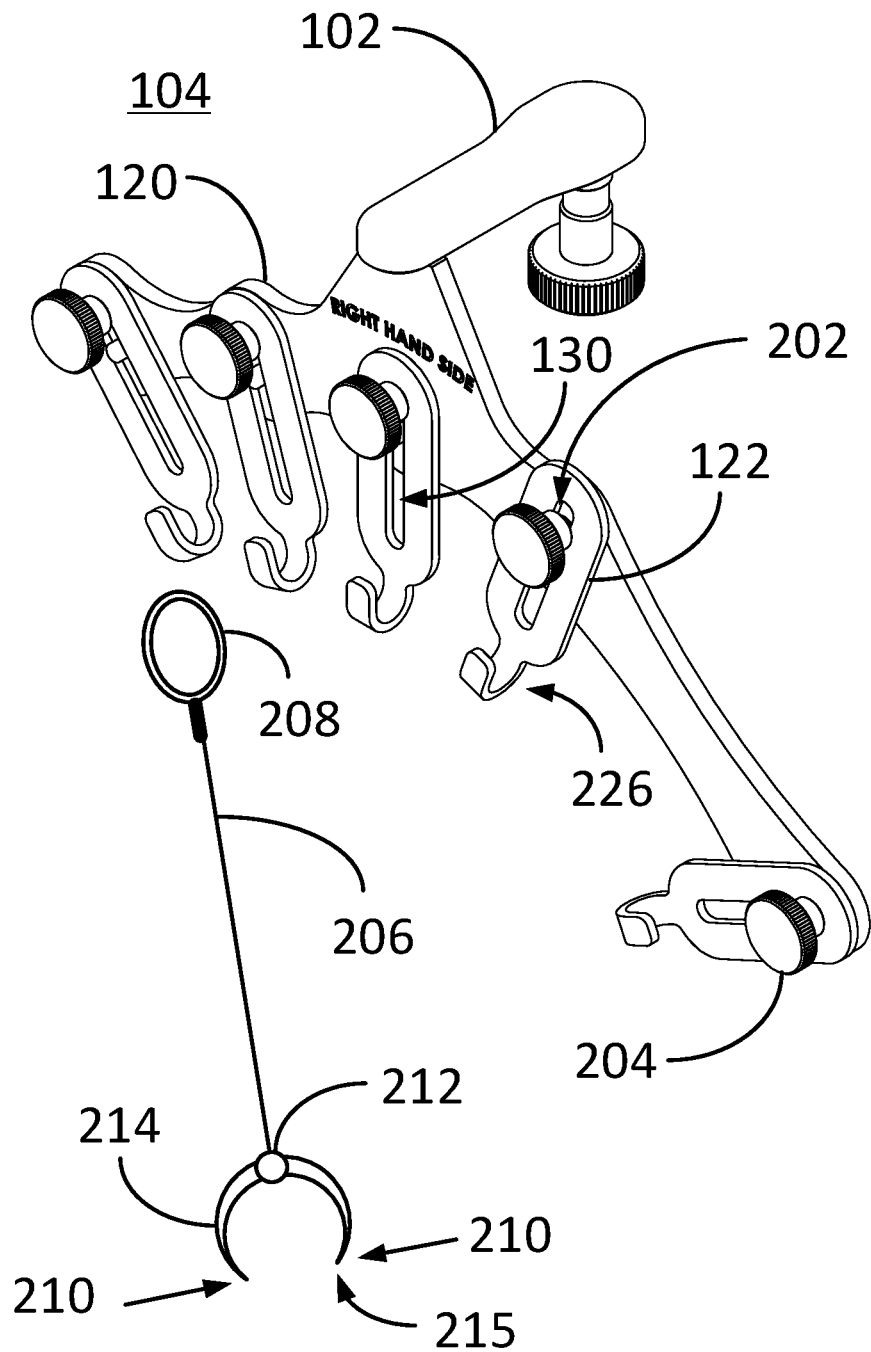
FIG. 2 depicts a perspective view of an embodiment of a hand suspension fixture consistent with embodiments of the present invention.

FIG. 2 depicts a perspective view of an embodiment of a hand suspension fixture 204 consistent with embodiments of the present invention. As shown in this embodiment, the retention fixtures 122 are set in place along the hand suspension fixture 104 by the knurled bolts 204. The knurled bolts 204 can be screwed in by hand and tightened against the arc shaped support plane 120, which provides mating threads to the knurled nuts 204. The retention fixtures 122 can pivot about the knurled bolts 204 or slid away or towards a hand (not shown) to be suspended. The retention fixture 122 positioned for an index finger, or second digit, is depicted partially slid away (see arrow 202) from where a human hand (not shown) is intended to reside. Each retention fixture 122 possesses a hook 226 adapted to receive a looped end 208 of a wire 206, or more generally a line, which is an embodiment of a flexible member 128. The wire 206 possesses a finger retention clamp 214 that is able to pivot around pivot point 212 to close pointed ends 215 around the sides of the distal phalange (last digit) of each finger in the direction of the arrows 210. Other embodiments contemplate a pair of needled ends penetrating the sides of the distal phalange of each finger, a tap or screw that penetrates into the bone from the sides of the distal phalange of each finger, or some other mechanism strong enough to hang a human hand by the fingertips from the hand suspension fixture 104.

Figure 3:
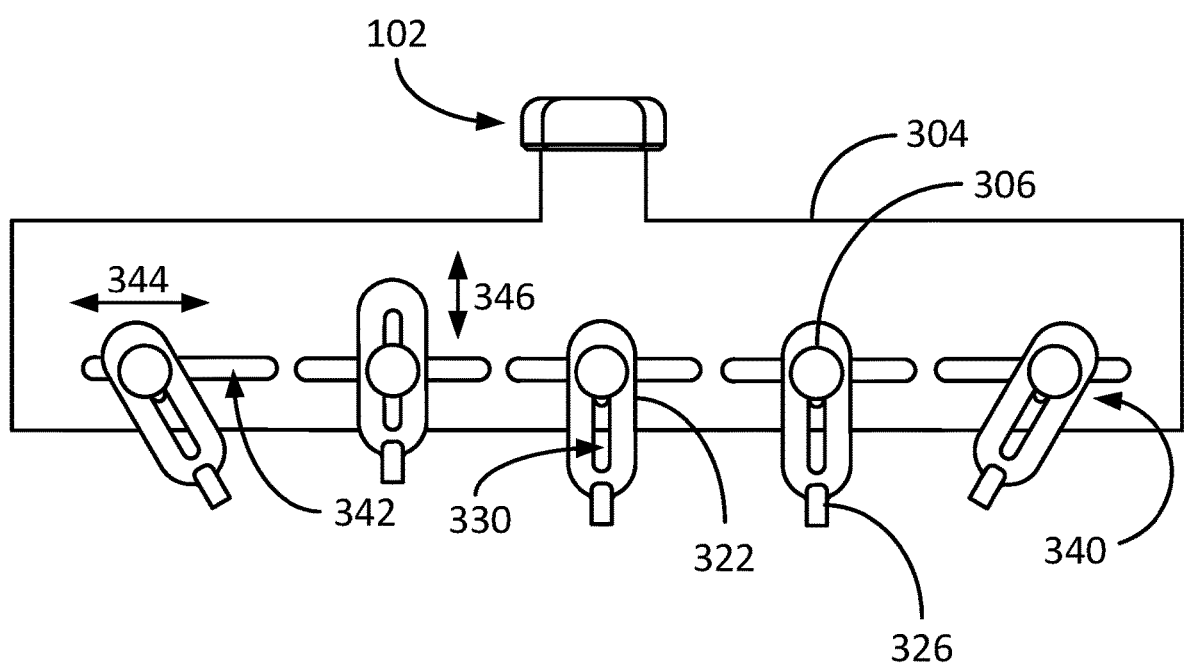
FIG. 3 illustratively depicts yet another embodiment of a hand suspension fixture consistent with embodiments of the present invention.

FIG. 3 depicts yet another embodiment of a hand suspension fixture 304 consistent with embodiments of the present invention. As depicted, the retention fixtures 322 are set in place along the hand suspension fixture 304 by locking mechanisms 306, which certain embodiments contemplate could be a finger tightening bolts, nut, quick release, or other mechanical locking mechanism known to those skilled in the art. Each retention fixture 322 is able to pivot around the locking mechanism 306 as shown by the retention fixture 340. Each retention fixture 322 is further able to slide towards or away from the suspended hand (not shown in this figure) via the retention fixture slot 330 as depicted by the double-arrow 346. Each retention fixture 322 is also able to slide horizontally along the hand suspension fixture 304 via hand suspension fixture slots 342 as shown by the double-arrow 344. Each retention fixture 322 also comprises a flexible member attachment location 326, such as a hook that a wire can loop around, for example.

Figure 4:
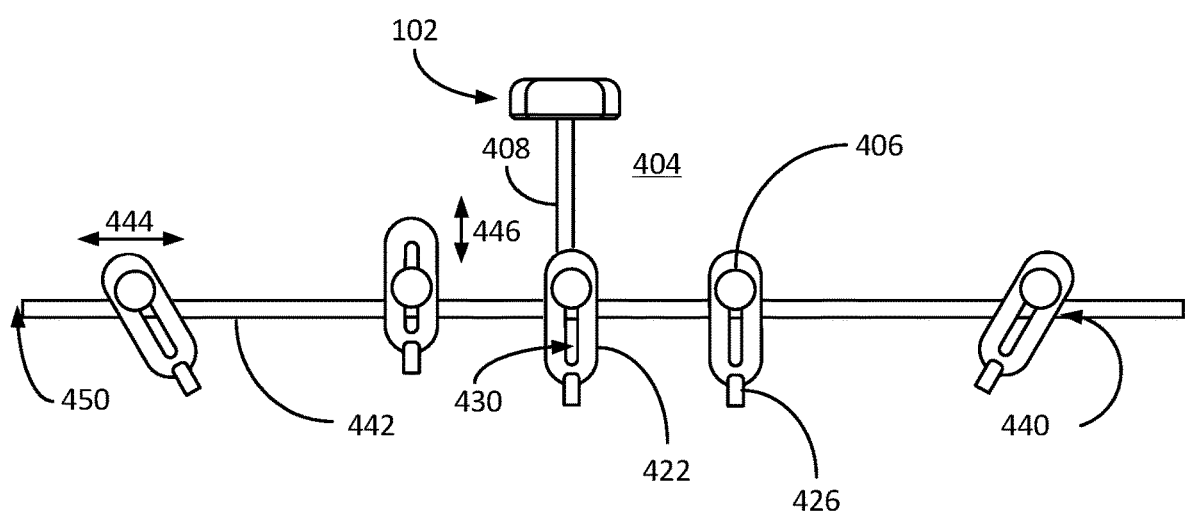
FIG. 4 illustratively depicts yet another alternative embodiment of a hand suspension fixture consistent with embodiments of the present invention.

FIG. 4 depicts yet another alternative embodiment of a hand suspension fixture 404 consistent with embodiments of the present invention. As shown, the retention fixtures 422 are slidingly engaged along a retention fixture bar 442 by locking mechanisms 406, which in one embodiment could be a sleeve that wraps around at least a part of the retention fixture bar 442 that can be tightened by hand via a knurled nut or bolt. In this embodiment, the retention fixtures 422 are capable of moving along the length of the retention fixture bar 442 as depicted by the double-arrow 444. The retention fixtures 422 are further capable of sliding towards or away from a hanging hand (not shown in this figure) via the retention fixture slot 430 as depicted by the double-arrow 430. Also, the retention fixtures 422 are capable of rotating about the locking mechanism 406, as shown by the retention fixture 440. Each retention fixture 422 comprises a flexible member attachment location 426, such as a hook (226) that a wire can loop around, for example. The hand suspension fixture 404 can be attached to a boom stand, or other support fixture, via element 102, to provide a stable support for the hand suspension fixture 404 to suspend a hand 110 and likely the weight of an arm. The stand can be set on the floor, hung from a ceiling, attached to furniture, such as a bed or table, for example. A hand suspension fixture vertical member 408 can be fixedly attached to the retention fixture bar 442, such as from behind the far 442, so as not to obstruct movement of the retention fixtures 422. Alternative embodiments contemplate a hand suspension fixture member supporting the retention fixture bar 442 at one or more of the retention fixture bar ends 450.

Figure 5:
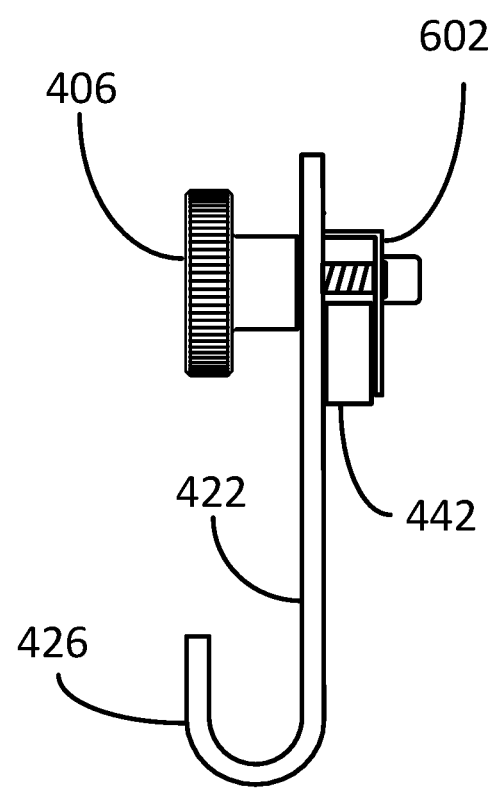
FIG. 5 depicts a side view/cut away embodiment that can be viewed in conjunction with FIG. 4 consistent with embodiments of the present invention.

FIG. 5 depicts a side view/cut away embodiment that can be viewed in conjunction with FIG. 4 consistent with embodiments of the present invention. As shown, the retention fixture 422 is fixedly attached to the retention fixture bar 442 via a sleeve 602 that partially wraps around the retention fixture bar 442. The sleeve 602 is tightened (or loosened) on the retention fixture bar 442 via the knob and bolt system 406. In this way, the retention fixture 422 can slide horizontally along the length of the retention fixture bar 442. Also, shown for reference is an embodiment of the retention fixture attachments location 426, which as a hook adapted to receive a looped portion of a flexible member 206.

Figure 6:
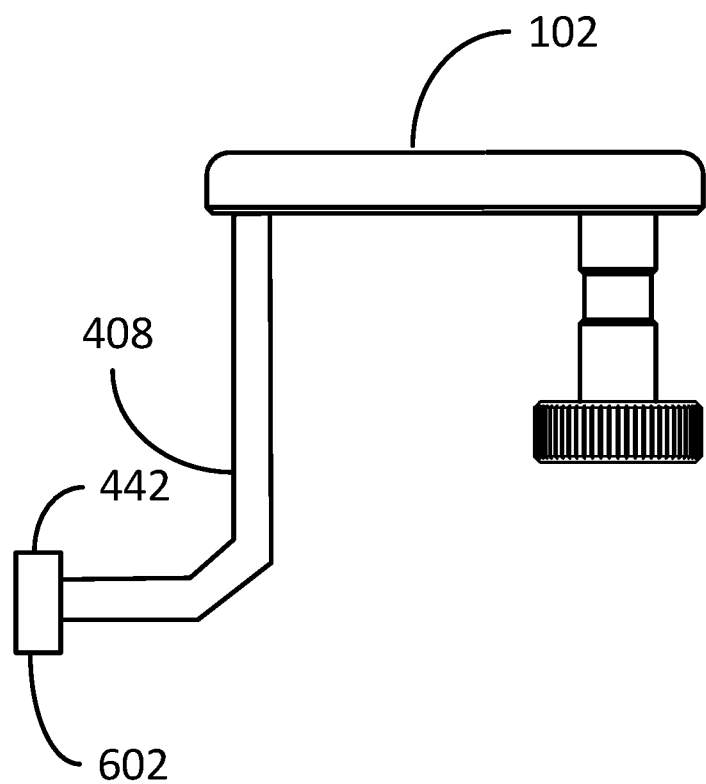
FIG. 6 illustratively depicts the side view of an embodiment of a suspension fixture vertical member consistent with embodiments of the present invention.

FIG. 6 illustratively shows the side view of an embodiment of a suspension fixture vertical member 408 consistent with embodiments of the present invention. The suspension fixture vertical member 408 is fixedly attached to the retention fixture bar 442, such as by welding, or screwed/bolted in place, for example. The suspension fixture vertical member 408 extends behind the retention fixture bar 442, but could just as easily be attached to the bottom of the retention fixture bar 602 in a way that would not obstruct sliding of a retention fixture 422. The hand suspension fixture support 102 is shown for reference.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, optional configurations for retention fixtures are conceivable or various ways of attaching a flexible member such as a wire or polymer line to the retention fixtures will be apparent to those skilled in the art while still maintaining substantially the same functionality without departing from the scope and spirit of the present invention. Other examples can include various shaped hand suspension fixtures, various shaped horizontal slots which could be arc shaped or optionally one long slot, such as slot 342 depicted in FIG. 3 while still maintaining substantially the same functionality without departing from the scope and spirit of the present invention. Further, though alternative embodiments such as a retention fixture bar 442 is shown, for example, other shaped bars the facilitate retention fixtures to move across the bar is conceivable without departing from the scope and spirit of the present invention. Additionally, though the embodiments described herein are directed to hanging all five digits (fingers) of a hand (including thumbs), it is envisioned that the hand can be supported by less than five fingers, such as two or three, for example without departing from the scope and spirit of the present invention.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

It is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A method for using a hand suspension system with a burned hand, the method comprising:
   providing a support beam with at least a first retention fixture, a second retention fixture, and a third retention fixture spaced apart being spaced apart on the support beam;
   connecting a first end of a first flexible line to a first distal end of a first burned human finger, a first end of a second flexible line to a second distal end of a second burned human finger, and a first end of a third flexible line to a third distal end of a third burned human finger;
   linking a second end of the first flexible line to the first retention fixture, a second end of the second flexible line to the second retention fixture, and a third end of the third flexible line to the third retention fixture; and
   suspending the burned hand vertically from the support beam with the first burned human finger, the second burned human finger and the third burned human finger, being spaced apart from one another.

2. The method of claim 1 wherein the first end of the first flexible line is connected to the first distal end of the first burned human finger via a distal digit connector, the distal digit connector connecting to only the first distal end of the first burned human finger.

3. The method of claim 2 wherein the distal digit connector is a finger retention clamp comprising a tap that penetrates into bone from either side of the first distal end of the first burned human finger.

4. The method of claim 1 further comprising wrapping each of the first burned human finger, the second burned human, and the third burned human finger with a skin graft, the skin graft from the first burned human finger being spaced apart from that of an adjacent one of the burned human fingers when the burned hand is suspended from the hand suspension system.

5. The method of claim 1 wherein the first retention fixture, the second retention fixture, and the third retention fixture are defined in a plane which positions the first burned human finger, the second burned human, and the third burned human finger to be spaced apart in the plane.

6. The method of claim 1 further comprising pivoting the first retention fixture, the second retention fixture, and the third retention fixture to accommodate the human fingers in a splayed configuration when the burned hand is being suspended from the hand suspension system.

7. The method of claim 1 further comprising attaching the hand suspension system to a stand.

8. The method of claim 1 wherein the linking step is accomplished by hooking a hook attached to each of the flexible lines to a corresponding retention fixture of the retention fixtures.

9. The method of claim 1 further comprising connecting a fourth end of a fourth flexible line to a fourth distal end of a fourth burned human finger and a fifth end of a fifth flexible line to a fifth distal end of a burned thumb; linking a second end of the fourth flexible line to a fourth retention fixture attached to the support beam and linking a fifth end of the fifth flexible line to a fifth retention fixture attached to the support beam, the burned hand comprising the fourth burned human finger and the burned thumb.

10. The method of claim 9 wherein none of the burned human fingers or the burned thumb are in contact with one another.

11. The method of claim 1 further comprising adjusting each of the first retention fixture, the second retention fixture, or the third retention fixture towards or away from one another along the support beam.

12. The method of claim 1 wherein the linking step is accomplished via a hook and loop relationship.

13. A method to hang a human hand vertically from a hand suspension system, the method comprising:
   providing the hand suspension system with a support beam comprising at least three retention fixtures spaced apart on the support beam between a first beam end and a second beam end;
   providing a first flexible line with a first finger connector at one end;

attaching a first finger connector to only a first distal end of a first burned finger, a second finger connector to only a second distal end of a second burned finger, and a third finger connector to only a third distal end of a third burned finger, a first flexible line extending from the first finger connector, a second flexible line extending from the second finger connector and a third flexible line extending from the third finger connector;

linking the first flexible line to a first of the at least three retention fixtures, a second flexible line to a second of the at least three retention fixtures, and a third flexible line to a third of the at least three retention fixtures;

wrapping each of the first burned finger, the second burned finger, and the third burned finger with a skin graft; and suspending the human hand from the support beam with the first burned finger, the second burned finger and the third burned finger being spaced apart from one another.

14. The method of claim 13 wherein the first finger connector is a finger retention clamp comprising a tap that penetrates into bone from either side of the first distal end of the first burned finger.

15. The method of claim 13 wherein the first flexible line links to the first of the at least three retention fixtures by way of a hook retained within a loop.

16. The method of claim 15 wherein the loop is at one end of the first flexible line.

17. A method to suspend a hand vertically from a hand suspension system, the method comprising:

providing the hand suspension system with a support beam with five adjustable retention fixtures disposed in a spaced apart arrangement along the support beam;

attaching a first distal end of a first finger to a first finger connector, a second distal end of a second finger to a second finger connector, and a third distal end of a third finger to a third finger connector, the first finger connector connected to a first flexible member, the second finger connector connected to a second flexible member, and the third finger connector connected to a third flexible member;

connecting the first flexible member to a first adjustable retention fixture, connecting the second flexible member to a second adjustable retention fixture and connecting the third flexible member to a third adjustable retention fixture;

splaying apart the first finger, the second finger, and the third finger via the spaced apart five adjustable retention fixtures while suspending the hand from the support beam via the first finger, the second finger, and the third finger, while being splayed apart no portion of any of the fingers touch one another.

18. The method of claim 17 wherein the support beam resides in a plane and the first finger, the second finger and the third finger are splayed apart in the plane when being suspended from the hand suspension system.

\* \* \* \* \*